(12) United States Patent
Zombo et al.

(10) Patent No.: US 7,060,971 B2
(45) Date of Patent: Jun. 13, 2006

(54) REFERENCE STANDARD SYSTEMS FOR THERMOSONIC FLAW DETECTION

(75) Inventors: Paul Zombo, Cocoa, FL (US); Paul Vona, Cocoa, FL (US); Miguel A. Felix, Irwin, PA (US)

(73) Assignee: Siemens Westinghouser Power Corporation, Orlando, FL (US)

( * ) Notice: Subject to any disclaimer, the term of this patent is extended or adjusted under 35 U.S.C. 154(b) by 698 days.

(21) Appl. No.: 10/243,009

(22) Filed: Sep. 13, 2002

(65) Prior Publication Data

US 2004/0051035 A1 Mar. 18, 2004

(51) Int. Cl.
*G01D 18/00* (2006.01)
*G01N 25/72* (2006.01)

(52) U.S. Cl. .................. 250/252.1; 250/341.1; 250/341.6; 374/5

(58) Field of Classification Search .......... 250/252.1, 250/341.6, 341.1; 374/5
See application file for complete search history.

(56) References Cited

U.S. PATENT DOCUMENTS

| | | | |
|---|---|---|---|
| 4,466,270 A | | 8/1984 | Kimura et al. |
| 4,660,419 A | * | 4/1987 | Derkacs et al. ............. 73/622 |
| 4,729,235 A | | 3/1988 | Podlech |
| 5,163,027 A | | 11/1992 | Miller et al. |
| 5,287,183 A | | 2/1994 | Thomas et al. |
| 5,408,883 A | | 4/1995 | Clark, Jr. et al. |
| 5,711,603 A | * | 1/1998 | Ringermacher et al. ....... 374/5 |
| 5,837,880 A | | 11/1998 | Shakinovsky et al. |
| 6,236,049 B1 | * | 5/2001 | Thomas et al. .......... 250/341.6 |
| 6,394,646 B1 | * | 5/2002 | Ringermacher et al. ....... 374/7 |
| 6,698,288 B1 | * | 3/2004 | Shirzad et al. ............. 73/577 |
| 2002/0172410 A1 | * | 11/2002 | Shepard .................. 382/141 |
| 2003/0010123 A1 | * | 1/2003 | Bates ..................... 73/606 |
| 2004/0041096 A1 | * | 3/2004 | Sun et al. ............. 250/341.6 |
| 2004/0089812 A1 | * | 5/2004 | Favro et al. ........... 250/341.6 |

* cited by examiner

*Primary Examiner*—Albert Gaglairdi

(57) ABSTRACT

A flaw inspection system (10) contains a substrate (12) to be inspected, such as a generator tube wall, a rotor of a generator, an aircraft skin, having or thought to have interior defects (24, 26) such as stress cracks, where the substrate (12) has attached reference blocks (14, 16) also containing defects (18, 20) of the type that might be found in the substrate, where an ultrasonic generator (28) emits sound waves (30) which contact all the defects, causing heat (32) which is sensed by a thermal camera (50) which, in association with a controller (54) causes images (60, 62) to appear on a monitor (52) from which the type and number of defects (24, 26) in the substrate (12) can be determined.

23 Claims, 3 Drawing Sheets

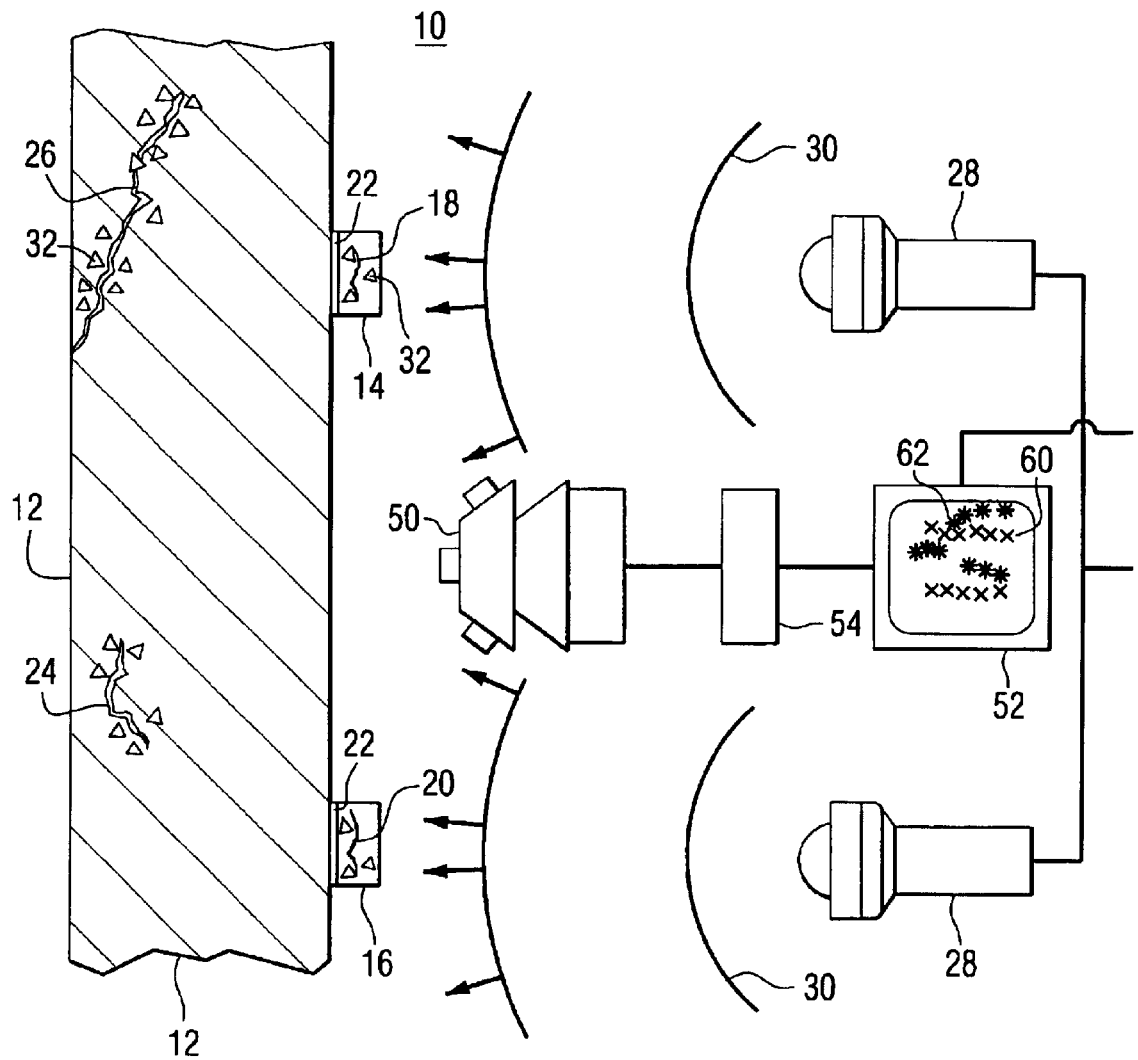
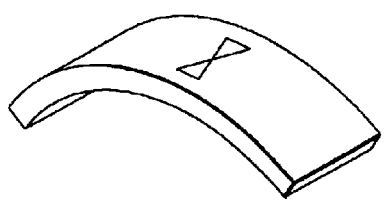
FIG. 2
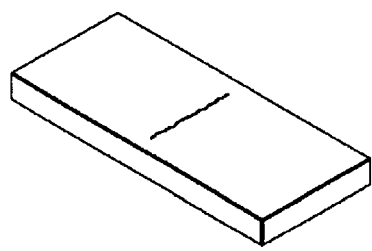
FIG. 3

REFERENCE STANDARD SYSTEMS FOR THERMOSONIC FLAW DETECTION

BACKGROUND OF THE INVENTION

1. Field of the Invention

This invention relates to a system and method of locating defects in a sample substrate by utilizing acoustic energy to generate a thermal signal that can be interpreted by an infrared detector and matching that thermal signal with a similar signal from a reference block applied directly to the sample.

2. Description of the Prior Art

In industries such as the turbine generator, aircraft, and many others, it is extremely important to maintain high standards of quality control because of safety concerns. It is important to be able to test machinery or aircraft parts for defects, such as pits, voids, corrosion, minor internal fractures and even service induced cracks, as in U.S. Pat. Specification No. 5,408,883 (Clark, Jr. et al.). There, a movable robotic diagnostic sampling device with ultrasonic and other type probes were used to monitor corrosion and potential cracks in heat exchanger tubes and the like in nuclear steam generators used in nuclear power plants. The sampling device could also cut a window in the tube wall and retrieve the sample window for mounting onto a separate tube for testing. The preferable way to monitor such problems, however, is on an assembly line before assembly and service. Preferably any tests would be non-invasive.

Much thought has been brought to the area of ultrasonic flaw detection and establishment of reference standards which contain flaws which potentially could be in the substrate to be tested. U.S. Pat. Specification No. 4,466,270 (Kimura et al.), relates to a reference block having an ultrasonic absorber attached to its back, for use in an ultrasonic examination method. This patent relates to a variation of a distance amplitude or area amplitude reference block used in pulse-echo ultrasonic flaw detection, where the reference discontinuity is a void within the reference block. When ultrasonic waves reach the back of the block they are partly transmitted to the absorber, where the ultrasonic energy is converted to heat energy and does not interfere with later, new ultrasonic pulses. This process results in decreased ghost interference on newer oscilloscope screens that use increased pulse repetition frequencies for automatic examination.

Other art in this area include, for example, U.S. Pat. Specification No. 4,729,235 (Podlech), related to a bonded specimen with intentionally placed, very small, discontinuities at the diffusion welded bond joint, that is also designed to provide reflectors in the path of ultrasonic waves which will produce the standard response on a time base ultrasonic sweep, and U.S. Pat. Specification No. 5,163,027 (Miller et al.) related to a standard calibration block incorporating a sequence of reflective interfaces designed to quantify the amplitude of the reflected ultrasonic energy with standard pulse-echo ultrasonic equipment. Also, U.S. Pat. Specification No. 5,837,880 (Shakinovsky et al.) which is a variation of the industry standard reference block, again, containing deliberately included features designed to be detected because they reflect ultrasonic energy back to a piezoelectric transducer. Reflectors are either voids or outer surfaces of the block.

None of this art appears to provide a thermal signal for detection by a thermal imaging camera. However, Thomas et al. in U.S. Pat. Specification No. 6,236,049B1 utilized an ultrasonic transducer coupled to an actual component, which might have a defect, through a malleable coupler, where the ultrasonic pulse energy from the transducer caused the defects, such as cracks, in the component to energize/heat up, such as by crack surfaces rubbing against each other so that thermal cameras could detect the defects or discontinuities from the heat, which appears as bright spot on the camera. Very short, even enclosed cracks as short as 0.75 mm are detectable by this method. This patent is an improvement of U.S. Pat. Specification No. 5,287,183 (Thomas et al.) which was an earlier system that was not as sensitive as the later Thomas et al. patent.

The component could be an in-use, or at rest aircraft fuselage, turbine blade component, rotor, vehicle cylinder head, or the like. The ultrasonic pulses used to heat cracks and defects in the 6,236,049B1 patent were simple pulses having substantially constant amplitude and did not need to employ sinusoidal signal modulation as used in vector lock in synchronous imaging.

This system allows detection of small cracks and tightly closed cracks. The problem with this system is, however, that it may not be particularly useful without reference standards or a means of characterizing defects appropriate reference standards designed specifically for this system.

Therefore a need has arisen to provide appropriate reference blocks/standards for use with a system that generates thermal signals for a thermal imaging camera from heat generated within a reference block/standard from ultrasonic pulse energy contact with a defect.

SUMMARY OF THE INVENTION

Accordingly it is a main object of this invention to provide appropriate reference blocks that can be applied directly to the sample under investigation to compare the thermal signal from both the reference block and the sample. Preferably, such reference blocks would be highly mobile, so that small, flawed reference blocks can be located and relocated at many areas of interest on the actual test specimen and viewed simultaneously during examination of the specimen.

These and other objects, advantages and features are achieved, by providing a method for analyzing flaws in a test specimen using flawed thermosonic reference blocks attached to the specimen, the method comprising: (a) providing a test specimen possibly containing or actually thought to contain or containing flaws: (b) attaching at least one reference block containing flaws similar to that which might be or are present in the test specimen; (c) contacting the test specimen with ultrasonic energy, with a portion of that energy being transmitted to the flawed reference block due to the attachment, where the ultrasonic energy generates heat at flaw locations; and (d) sensing any heat generated in the test specimen and the flawed reference block by a thermal imaging apparatus which generates images on a monitor, where images from the test specimen and the flawed reference block can be observed with the flawed reference block being used as an indicator of ultrasonic energy transmission into the test specimen. Here the attachment is effected by a suitable coupling material.

The invention also resides in a thermosonic system comprising: (a) a test specimen possibly containing or actually thought to contain or containing flaws; (b) at least one reference block containing flaws similar to that which might be or are present in the test specimen attached to the test specimen; (c) an ultrasonic energy generator capable of passing ultrasonic energy to the test specimen such that a portion of that energy is transmitted to the flawed reference block due to the attachment; and (d) a thermosonic thermal imaging apparatus capable of sensing heat from the test specimen and the flawed reference block and generating images on a monitor related to said sensed heat such that any said images from the test specimen can be compared to images from the flawed reference block. Here, attached includes coupled by a suitable coupling material.

The flaws can be scales, minor internal fractures, stress cracks, minor imperfections which could develop into stress cracks, and the like. The flaw in the reference blocks would be determined by each test specimen and what potential flaws the test specimen might contain. The reference blocks could be attached directly to the test specimen by a coupling of at least one of a thin layer of adhesive, magnetism, spring clip, or the like, which would not affect sound waves passing through it or by brazing technique. The reference block would preferably be the same composition as the test specimen and would preferably be from about 0.1 cm to 1.5 cm thick, preferably 0.1 to 0.5 cm thick.

BRIEF DESCRIPTION OF THE DRAWINGS

In order that the invention will be more clearly understood, convenient embodiments thereof will now be described by way of example, with reference to the accompanying drawings, in which:

FIG. 1, which best shows the invention, is a view partially in section of one embodiment of the operation of the thermosonic inspection system of this invention, showing a test specimen wall, partially in section for the sake of clarity, having stress crack defects, being monitored by reference blocks, having flaws similar to those in the wall, directly attached to the wall and also showing a thermal camera system;

FIG. 2 is a perspective view of one embodiment of a reference block with a notch machined into its top curved surface;

FIG. 3 is a perspective view of the reference block shown in FIG. 2 after straightening;

DESCRIPTION OF THE PREFERRED EMBODIMENTS

Figure 4:
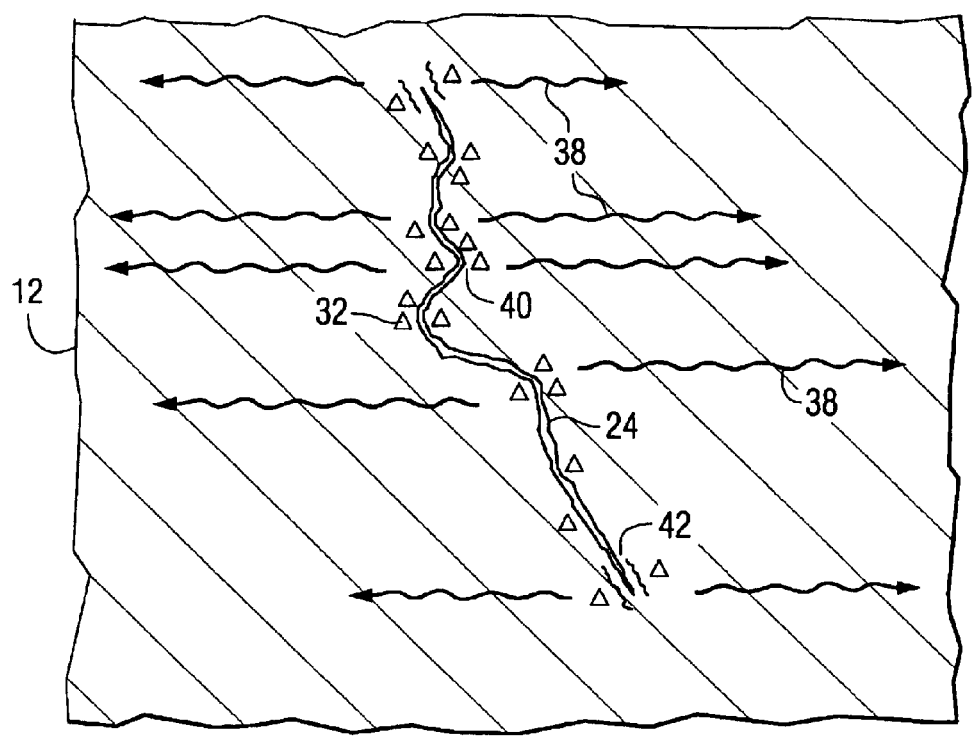
FIG. 4 is a cross-sectional enlarged view of the bottom stress crack defect shown in FIG. 1 showing possible thermosonic effects and/or plastic deformation effects at the stress crack site.

The general principals of infrared imaging of ultrasonically excited subsurface defects in samples is taught by Thomas et al. in U.S. Pat. Specification No. 6,236,049B1, herein incorporated by reference. There, an ultrasonic source was connected to a specimen being inspected through a coupler that transmitted the ultrasonic waves into the material with minimum attenuation. The ultrasonic source emitted a single ultrasonic pulse having a constant frequency and amplitude for a predetermined period of time. A suitable thermal imaging camera was used to image the specimen when it was being excited by the ultrasonic source. A control unit was used to control the operation of the ultrasonic source and the camera for timing purposes. During initiation of the detection sequence, the control unit instructed the camera to begin taking sequential images of the specimen. Next, the control unit instructed the transducer to emit a pulse of ultrasonic energy at a predetermined frequency for a predetermined time period. A sequence of images were generated that show cracks and other defects in the material as light areas (higher temperature) against a dark (lower temperature) background. The images were displayed on a monitor, and a storage device was provided to store the sequence of images to be reviewed at a later time. A controller provided timing between a transducer and a camera. The controller could be any computer suitable for the purposes. When the detection process was initiated, the controller caused the camera to begin taking sequential images of the specimen at a predetermined rate. Once the sequence of images began, the controller sent a signal to an amplifier that caused the amplifier to send a pulse to the transducer to generate a pulsed ultrasonic signal. The ultrasonic energy was in the form of a simple pulse at the frequency being used. After the end of the pulse, the controller instructed the camera to stop taking images. The images generated by the camera were sent to a monitor that displayed the images of the side of the specimen. The images can then be sent to a storage device to be viewed at another location if desirable.

It was thought that the ultrasonic energy applied to the specimen caused faces of the defects and cracks in the specimen to rub against each other and create heat. This heat appeared as bright spots in the images generated by the camera. For those cracks that may be open, where the faces of the crack do not touch, the heating was thought to be generated as the stress concentration point at the crack tip. The ultrasonic energy was effective to heat the crack of defect in the specimen no matter what the orientation of the crack was relative to the energy pulse.

Referring now to FIG. 1, a thermosonic referencing/inspection system 10 is shown, containing a test specimen 12, which, generally has just been manufactured, or is a service run component which might contain flaws, and is being tested for quality control. The type specimens being tested would be the type where failure could cause safety problems, for example, heat exchanger tubes and other metal components used in nuclear and other type generators, aircraft parts, aerospace, automotive, manufacturing, electronics, marine, construction parts and the like.

Figure 5:
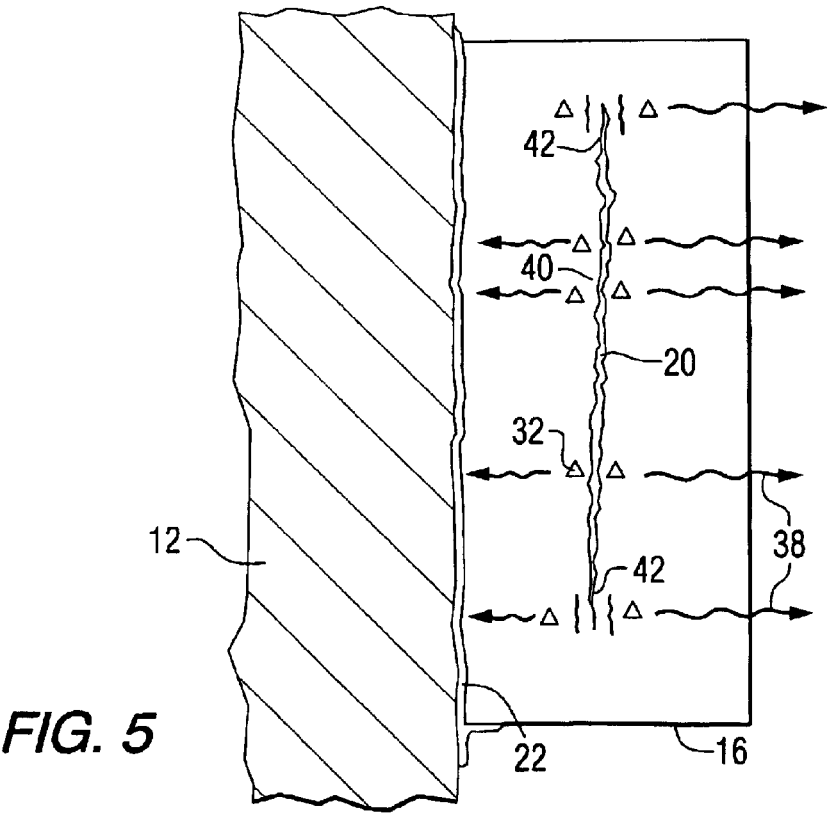
FIG. 5 is a cross-sectional enlarged view of the bottom attached reference block showing possible thermosonic effects and/or plastic deformation effects at the induced stress crack site.

One or more reference blocks/standards 14 and 16 are shown, which do contain flaws 18 and 20 which might be present in the type test specimen being tested. These reference blocks/standards 14 and 16 are directly attached to the test specimen 12 by an adhesive, brazing layer, magnetism, spring clip, or the like couple 22, which will not interfere with sonic transmissions. FIG. 5 shows a magnified cross-section of reference block 16. The particular flaws 24 and 26 shown in the test specimen 12 are, for illustration only, small cracks. Generally speaking voids, pits, porosity and other open gross discontinuities are not well suited to this examination method unless they have a defect with contacting surfaces associated with them. The discontinuities that favor thermosonics are cracks, laminations, bond-line issues, and other types of discontinuity that either allows for the friction of faying surfaces or the stress concentration at notch areas.

Ultrasonic energy generator (s) 28 can be an ultrasonic transducer of any suitable type which generates a pulse of ultrasonic energy having a constant amplitude at a frequency of from about 5–100 kHz for from about a fraction of a second to 5 seconds at a power level of from about 50 W to 3 kW. It can impart ultrasonic pulses disposed away from the specimen or next to the specimen directly or through an appropriate type of coupler material. Coupling media used in ultrasonic flaw detection is not well suited to the forces used/generated with this test method. Useful coupler/coupling material for thermosonics includes but is not limited to copper, brass, aluminum, lead and paper. The sonic waves, shown as 30, pass through/into the test specimen 12 and reference blocks 14 and 16 contacting any flaws 24 and 26 and causing an effect on the flaws, generating heat, shown as triangles 32 at or within or around the flaws, best shown in FIGS. 4 and 5.

The heat 32 generated passes as thermal waves, shown as arrows 38 propagating from the defect, as shown in FIGS. 4 and 5. The heat is thought to generate a thermal signal at opposing surfaces, such as 40, of cracks or crack-like features that are in contact and which rub together, causing heat from friction. Another possibility is that there is a degree of plastic deformation at the extreme tips 42 of sharp fissures, and this deformation causes heat. The reference standards 14, 16 of this invention make use of these mechanisms. By attaching the reference pieces 14, 16 to the test article 12 under investigation, the acoustic energy is caused to be transmitted into the reference piece 14, 16 through the couple 22, and the discontinuities in the reference piece will behave in much the same fashion as any potential discontinuities in the test article. This will give some indication of the level of acoustic energy in the vicinity of the reference standard. Because not all items examined by the acoustic thermography method will have discontinuities, which is true of any examination method, removing and reattaching the reference pieces 14, 16 at various locations on the test article 12 will provide a measure of the effectiveness of the acoustic thermography examination over the entire surface (s) to be examined.

The heat 32 generated and passing as heat waves 38 is sensed by a thermosonic imaging apparatus 50 which may contain one or more thermal imaging cameras spaced any suitable distance to provide images of as much of the test specimen 12 and reference blocks 16 and 18 as desired. The camera in one useful embodiment senses infrared emissions in the 3–5 micrometer wavelength and generates images at about 100 frames per second at monitor 52 (shown as a series of x's). What will be seen in the monitor 52, as depicted in FIG. 1, will be a gray-scale representation of a thermal image as detected by the thermal imaging camera. Within this gray-scale image will be the test specimen with the attached reference standards. Upon energization of the ultrasonic source within the correct parameters for the mass and configuration of the test specimen, thermal signals will begin to appear at various points in time during the energization/image capture sequence. The interface between the ultrasonic sonotrode, if in the field of view, will 'light-up' as will the interface(s) between the reference standard(s) and test specimen, and any surface or near surface features that produce the mechanisms as described. In one instance images 60 associated with the flaws in the reference block show up on the monitor and can be compared to images 62 (shown as a series of asterisks*) associated with flaws in the test specimen.

A controller 54 provides timing between the ultrasonic energy generator 28 and the thermosonic imaging apparatus 50. The function of the controller has been discussed previously. The reference blocks/standards 14 and 16 for thermosonics would typically be small to maximize the view of the test component/specimen 12. Larger reference standards could also be used, however and if view obstruction is an issue, a coupling piece could allow the larger reference standard to be moved out of the line of sight. Preferably the reference blocks/standards are from about 1 square cm. to 2 square cm each and cover preferably less than about 1% of the test surface area. The thickness of the reference blocks is between about 0.01 cm and 1.5 cm, preferably 0.01 cm and 0.5 cm. Attachment of the reference standard would be made by mechanical, metallurgical or adhesive methods.

Reference standards could be manufactured in many forms with many flaw styles. Natural reference block/standards could be cut from service or mechanically tested components. These would be removed from the component. The flaw would be completely contained in a small reference standard. This could then be attached to the test specimen as witness to the examination effectiveness.

Manufactured reference standards could include thin sheet, cut into small shapes, with mechanically flaw or damage, induced by tensile, creep, fatigue, overload, corrosion or thermal quench flaws. Different reference standards could contain different sizes of flaws or multiple flaws of varied size or characteristics. Mechanically induced defects are natural flaws and therefore very representative of the test specimen defects. Manufactured reference standards could also include typical mechanical test standards. Tensil, creep, fatigue, thermal quench, and compact tensile standards could be used if not brought to ultimate failure. Much is known about the failure of mechanical specimens and therefore, defects could be grown with some accuracy in site or character. The defects would then be removed intact and shaped as needed to conform to the surface of the test specimen.

Standards could be manufactured purposely subjecting metal sheets to mechanical stresses that would induce desired flaws. Standards could also be obtained by acquiring mechanical test specimens that have not been tested to failure. These specimens can be manipulated in the test apparatus (such as a tensile machine) to grow the desired flaw. The flawed section could then be removed from the specimen and used as a reference standard. Another means would be to allow excess material on the test specimen that could be mechanically fatigued to grow flaws. These areas would then be machined away after testing.

New styles of reference standards could be made that have several key features for design criteria. One key feature could include size/contoured coupling surfaces and consideration of acoustic preparation like acoustic impedance, contact area and wavelength/tuning based size selection. The test specimen could incorporate grip or pin areas, or loading areas for the allowance of reference standard loading. These features may be removed by subsequent machining. To cause flaws, stresses may be applied internally or externally to the reference standard. The loading may be constant, varied or cyclic. The stresses may be applied by a combination of tension, shear or torsion. To simulate anticipated defects in the test specimen it may be necessary to reshape the specimen in the region of the flaw. This would allow the specimen optimum shape for sound coupling at the coupling region so the optimum shape for flaw characteristics in the region of the flaw. The advantages of using the reference standard include: proof of effective energization, identification of regions on a test component with weak acoustic energy density and first hand knowledge of the indication quality from a known flaw. Adhesive type indicators, constructed with differently shaped artificial debonds affixed to the adhesive side of tape, and with artificial flaws introduced into the simulated debond, can be used to gauge the effectiveness of the acoustic thermography energy through coatings of various materials.

Figure 6:
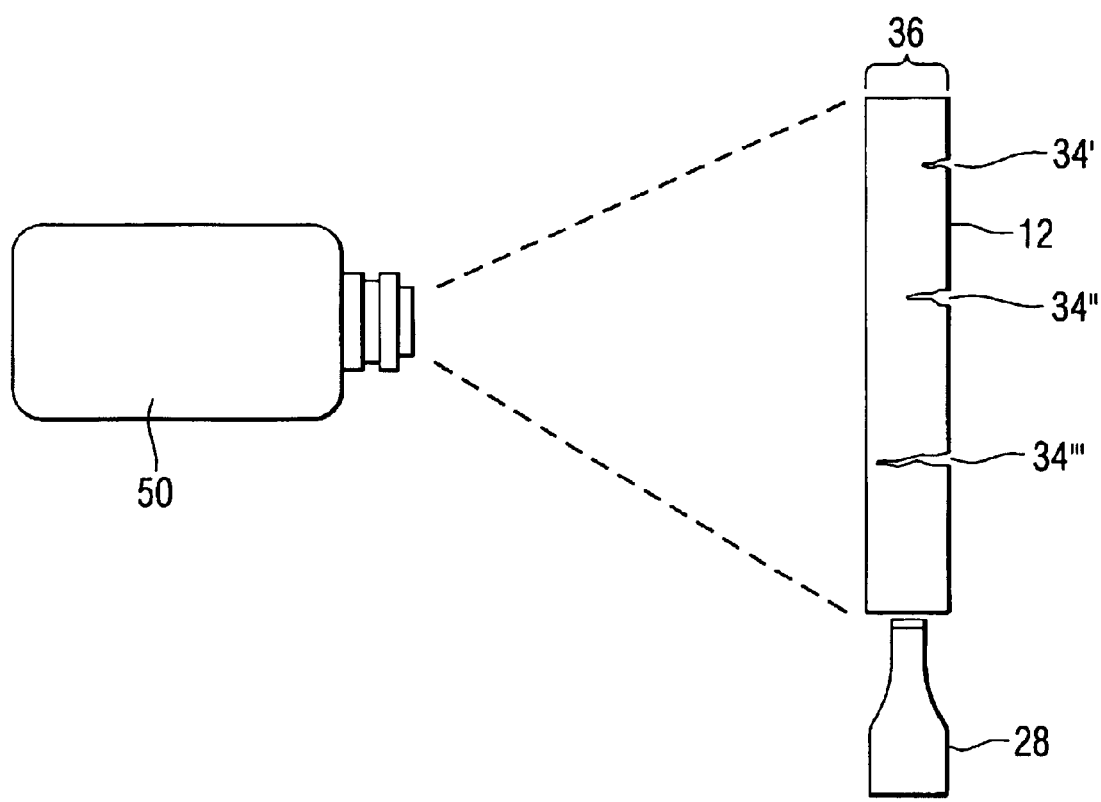
FIG. 6 is a view partially in section of operation of the thermosonic inspection system to determine depth sensitivity to subsurface defects.

Specimens with EDM notches, which are not normally detectable, could be modified by peening or other mechanical deformation to cause opposing major faces of the notch to contact each other. Also, the EDM notches could be introduced into a curved component as shown in FIG. 2, on the convex surface, and a subsequent rolling operation could be used to straighten the component forcing the faces of the notch together as shown in FIG. 3. Varying notch depths could be used to gauge system sensitivity by energizing from the reverse side. FIGS. 2 and 3 are intended to depict one possible method of producing reference features. Other methods could include thermal shock, fatigue, and the like. As shown in FIG. 6, by introducing notches 34', 34", 34''' of varying depth, and observing the panel from the surface opposite that of the notch opening(s), and indication of sensitivity to flaw depth can be obtained. For instance, if the reference panel is 4 mm thick, shown at 36, and three notches are introduced in one major surface, one 1 mm deep 34', and one 2 mm deep 34", and one 3 mm deep 34''', and the panel energized and the imaging camera 50 trained on the opposite major surface, if all three notches are observable, we know that flaws 3 mm deep are observable. However, if only the 3 mm notch is observable, then we can only see flaws 1 mm from the surface.

Adhesives such as a common tape substrate could demonstrate both effective energization and energy distribution. These can be very thin or moderately thick. The poorly bonded regions of adhesive heat up upon energization like crack and coating debond defects. If small and intentional debonds are located between the adhesive and the test component, the debond would only heat-up if the energization was successful. Taking this idea a step further, if a matrix of intentional debonds were attached to a strip of adhesive tape and the tape was located over a large region of a test component, this would serve as a means demonstrating energy distribution. Very thin adhesives may allow component examination through the adhesive.

While the invention has been described in terms of preferred embodiments, various changes, additions and modification may be made without departing from the scope of the invention as set forth in the following claims.

What is claimed is:

1. A method for analyzing flaws in a test specimen using flawed thermosonic reference blocks attached to the specimen, the method comprising:
   (a) providing a test specimen possibly containing or actually thought to contain or containing flaws;
   (b) attaching at least one reference block containing flaws similar to that which might be present or are present in the test specimen;
   (c) contacting the test specimen with ultrasonic energy, with a portion of that energy being transmitted to the flawed reference block due to the attachment, where the ultrasonic energy generates heat at flaw locations; and
   (d) sensing any heat generated in the test specimen and the flawed reference block by a thermal imaging apparatus which generates images on a monitor,
   where images from the test specimen and the flawed reference block can be observed with the flawed reference block being used as an indicator of ultrasonic energy transmission into the test specimen.

2. The method of claim 1, where the flawed reference block is attached by brazing techniques and the images can be compared to see if the images from the test specimen match the images from the flawed reference block.

3. The method of claim 1, where the flawed reference block is attached by at least one of a thin layer of adhesive, magnetism, and spring clip couples.

4. The method of claim 1, where heat is generated at the flaw location by flaw surfaces rubbing against each other.

5. The method of claim 1, where heat is generated at the flaw location by plastic deformation at the tip of a fissure.

6. The method of claim 1, where the flawed block is the same material as the test specimen and the ultrasonic energy is provided by a transducer which emits a single ultrasonic pulse having a constant frequency amplitude for a predetermined period of time.

7. The method of claim 1, where a thermal camera senses any heat generated by the ultrasonic energy and takes sequential images of the test specimen and the flawed reference block.

8. The method of claim 1, where a controller provides timing between the source of ultrasonic energy and the heat sensor.

9. The method of claim 1, where the thickness of the reference block is between about 0.1 cm and 1.5 cm.

10. The method of claim 1, where the thickness of the reference block is between about 0.1 cm and 0.5 cm.

11. A thermosonic system comprising:
    (a) a test specimen possibly containing flaws;
    (b) at least one reference block containing flaws similar to that which might be present in the test specimen attached to the test specimen;
    (c) an ultrasonic energy generator capable of passing ultrasonic energy to the test specimen such that a portion of that energy is transmitted to the flawed reference block due to the attachment; and
    (d) a thermosonic thermal imaging apparatus capable of sensing heat from the test specimen and the flawed reference block and generating images on a monitor related to said sensed heat,
    such that any said images from the test specimen can be compared to images from the flawed reference block.

12. The referencing system of claim 11, where the flawed reference block is attached by a brazed joint couple.

13. The referencing system of claim 11, where the flawed reference block is attached by at least one of a thin layer of adhesive, magnetism, and a spring clip couple.

14. The reference system of claim 11, where heat is generated at the flaw location by flaw surfaces rubbing against each other.

15. The reference system of claim 11, where heat is generated at the flaw location by plastic deformation at the tip of a fissure.

16. The referencing system of claim 11, where the flawed reference block is the same material as the test specimen and the ultrasonic energy generator is a transducer which emits a single ultrasonic pulse having a constant frequency amplitude for a predetermined period of time.

17. The referencing system of claim 11, where the thermal imaging apparatus is a thermal camera that senses any heat generated by the ultrasonic energy and takes sequential images of the test specimen and the flawed reference block.

18. The referencing system of claim 11, also containing a controller which provides timing between the ultrasonic energy generator and the thermal imaging apparatus.

19. The referencing system of claim 11, where the flawed reference block is a natural reference block from service or mechanically tested components.

20. The referencing system of claim 11, where the flawed reference block is a manufactured reference block with at least one mechanically induced flaw or damage induced by: tensile, creep, fatigue, overload, corrosion flaw or thermal quench flaws.

21. The referencing system of claim 11, where the flawed reference block is an adhesive tape substrate containing intentional debond flaws.

22. The method of claim 11, where the thickness of the reference block is between about 0.1 cm and 1.5 cm.

23. The method of claim 11, where the thickness of the reference block is between about 0.01 cm and 0.5 cm.

* * * * *